United States Patent
Liao et al.

(10) Patent No.: US 9,803,172 B2
(45) Date of Patent: Oct. 31, 2017

(54) METHOD FOR INDUCING BACTERIA TO ENTER INTO VIABLE BUT NONCULTURABLE STATE

(71) Applicant: CHINA AGRICULTURAL UNIVERSITY, Beijing (CN)

(72) Inventors: Xiaojun Liao, Beijing (CN); Feng Zhao, Beijing (CN)

(73) Assignee: CHINA AGRICULTURAL UNIVERSITY, Beijing (CN)

(*) Notice: Subject to any disclaimer, the term of this patent is extended or adjusted under 35 U.S.C. 154(b) by 0 days.

(21) Appl. No.: 14/436,031

(22) PCT Filed: May 31, 2013

(86) PCT No.: PCT/CN2013/000648
§ 371 (c)(1),
(2) Date: Apr. 15, 2015

(87) PCT Pub. No.: WO2014/059742
PCT Pub. Date: Apr. 24, 2014

(65) Prior Publication Data
US 2015/0267163 A1    Sep. 24, 2015

(30) Foreign Application Priority Data
Oct. 16, 2012    (CN) .......................... 2012 1 0392524

(51) Int. Cl.
*C12N 1/20*    (2006.01)
*C12N 1/04*    (2006.01)
*C12N 1/36*    (2006.01)

(52) U.S. Cl.
CPC ................ *C12N 1/20* (2013.01); *C12N 1/04* (2013.01); *C12N 1/36* (2013.01)

(58) Field of Classification Search
CPC .............. C12N 1/04; C12N 1/20; C12N 1/36
See application file for complete search history.

(56) References Cited

FOREIGN PATENT DOCUMENTS

CN    102899272 A    1/2013
WO    WO 02056824 A2 *    7/2002 ............ A61L 2/0011

OTHER PUBLICATIONS

Garcia-Gonzalez et al. (2007) International Journal of Food Microbiology 117: 1-28.*
Xu et al. (1982) Microb. Ecol. 8: 313-323.*
Yuk et al. (2010) International Journal of Food microbiology 138: 91-99.*
Bi et al. (2015) Food control 50: 705-713.*
The inducement and research on the "viable but non-culturable state" for three types of pathogenic bacteria. Mar. 2009.
Chinese office Action issued to Chinese Application No. 20121039524.0 dated Sep. 23, 2013.
Zhao, F., et al., "Induction of Viable but Nonculturable *Escherichia coli* O157:H7 by High Pressure CO2 and Its Characteristics," PLOS ONE, vol. 8, No. 4, e62388, pp. 1-8, Apr. 23, 2013.
Kincal, D., et al., "A Continuous High Pressure Carbon Dioxide System for Microbial Reduction in Orange Juice," Journal of Food Science, vol. 70, No. 5, pp. M249-M253, Oct. 6, 2005.
Yang, Zhen, "Master's Degree Thesis of Tianjin University of Science and Technology: The inducement and research on the 'viable but non-culturable state' for three types of pathogenic bacteria," CNKI, Master's Theses Full-Text Database, Dec. 18, 2009.
International Search Report dated Aug. 22, 2013 for PCT/CN2013/000648.

* cited by examiner

*Primary Examiner* — Lisa J Hobbs
(74) *Attorney, Agent, or Firm* — Knobbe Martens Olson & Bear, LLP

(57) ABSTRACT

A method induces bacteria to enter into viable, but nonculturable state. The method includes subjecting a target bacterium to high pressure carbon dioxide treatment so as to make it enter into the viable, but nonculturable state, which can be demonstrated experimentally. The viable but nonculturable state can be entered quickly, such as within one hour.

7 Claims, No Drawings

METHOD FOR INDUCING BACTERIA TO ENTER INTO VIABLE BUT NONCULTURABLE STATE

CROSS REFERENCE TO RELATED APPLICATIONS

This application is the U.S. National Phase of International Application No. PCT/CN2013/000648, filed May 31, 2013, designating the U.S. and published in Chinese as WO 2014/059742 on Apr. 24, 2014 which claims the benefit of Chinese Patent Application No. 201210392524.0, filed Oct. 16, 2012.

Any and all applications for which a foreign or domestic priority claim is identified here or in the Application Data Sheet as filed with the present application are hereby incorporated by reference under 37 CFR 1.57.

TECHNICAL FIELD

The present invention relates to the technical field of biological medicine, and particularly to a method for inducing bacteria to enter into a viable but nonculturable state.

BACKGROUND TECHNOLOGY

In a hostile environment, many bacteria will enter into a viable but nonculturable (VBNC) state. This state is a dormant form of non-sporulating bacteria, and may improve the survival of bacteria in a hostile environment. Currently, over 60 species of bacteria are known to be capable of entering into the VBNC state, most of which are pathogenic bacteria. The bacteria in the VBNC state still have metabolic activities, while cannot grow or form bacterial colonies on non-selective media commonly used for the bacteria. Therefore, conventional methods for bacteria detection, such as plate counting method, cannot detect the presence of bacteria in the VBNC state. As such, it is probably to underestimate the number of bacteria in a sample detected, bringing potential security risks to people. Therefore, conducting researches on the characteristic and formation mechanism of the bacteria in VBNC state is vitally important for effectively killing them. However, it takes a long time to obtain the bacteria in VBNC state, which thus limits the study progress thereof.

At present, the methods for inducing bacteria to enter into a viable but nonculturable state are primarily the method of oligotrophy combined with low temperatures. However, this method needs a long time for inducing, typically more than one month, thereby restricting the research progress of the bacteria in the VBNC state.

SUMMARY

The present invention aims at providing a method for inducing bacteria to enter into a viable but nonculturable state.

The present invention provides a method for inducing a target bacterium to enter into a viable but nonculturable state comprising: subjecting the target bacterium to high pressure carbon dioxide treatment, so as to make it enter into the viable but nonculturable state.

In the above method, the conditions of the high pressure carbon dioxide treatment are: a pressure of 5-7 MPa, a temperature of 25-37° C., and a time of 5-60 min.

In the above method, the conditions of the high pressure carbon dioxide treatment are as follows:

a pressure of 5 MPa, a temperature of 25° C., and a time of 40 min;

or a pressure of 5 MPa, a temperature of 31° C., and a time of 30 min;

or a pressure of 5 MPa, a temperature of 37° C., and a time of 25 min.

In an example of the present invention, the target bacterium is subjected to a high pressure carbon dioxide treatment using high pressure carbon dioxide equipment. In an example of the present invention, the model of the high pressure carbon dioxide equipment is CAU-HPCD-1 (a high density of carbon dioxide sterilization equipment, disclosed in the patent ZL200520132590.X), and the specific steps are: 20 mL of bacteria liquid to be induced (bacteria suspension) was put into a glass bottle, and sealed with a sealing film; the bacteria liquid was put into a reaction kettle, and treated with HPCD at a pressure of 5 MPa and a temperature of 25° C., with the pressure being held for 40 min; and the kettle was immediately depressurized when the above treating parameters were achieved; the induced bacteria liquid was thus obtained.

Prior to the high pressure carbon dioxide treatment, the above method further comprises the following step: washing and suspending the target bacterium to obtain the bacteria suspension.

In the above method, a physiological saline is used for both the washing and the suspending, and the physiological saline is specifically a 0.85% (w/v) NaCl aqueous solution.

In the above method, the target bacterium is a target bacterium in exponential phase.

In the above method, the target bacterium is *Escherichia coli*, and the *Escherichia coli* is specifically *Escherichia coli* O157:H7.

After the high pressure carbon dioxide treatment, the above method further comprises the following steps: detecting the number of viable bacteria and culturable bacteria of the target bacterium after an inducing treatment; if the number of culturable bacteria is zero but the number of viable bacteria is not, the target bacterium enters into a viable but nonculturable state; wherein, the PI/SYTO 9 double staining method is used for detection of the number of viable bacteria of the target bacterium after the inducing treatment, and the plate counting method is used for the detection of the number of culturable bacteria of the target bacterium after the inducing treatment.

Another purpose of the present invention is to provide a method for culturing bacteria.

The method for culturing bacteria provided by the present invention comprises the steps of the above method.

DETAILED DESCRIPTION OF CERTAIN EMBODIMENTS OF THE INVENTION

All the experimental methods used in the following examples, if not specifically indicated, are conventional methods.

All the materials and reagents, etc. used in the following examples, if not specifically indicated, can be obtained by a commercial way.

The present invention is further described combining with Examples as follows. The above examples are merely used to describe and not limit the technical solutions of the present invention. In spite of the detailed description of the present invention with referring to the preferred embodiments, it should be appreciated by ordinary skill in the art that modifications or equivalent replacements on the technical solutions of the present invention can be made without departing from the spirit and scope of the technical solutions of the present invention, and should be covered in the scope of claims of the present invention.

EXAMPLE 1

Inducing Bacterium to Enter into a Viable but Nonculturable State

I. Induction by High Pressure Carbon Dioxide.
1. Preparation of Bacterial Suspension.
   *Escherichia coli* O157:H7 (strain No. NCTC12900) in exponential growth phase was washed twice with 0.85% (w/v) NaCl aqueous solution, and then resuspended in 0.85% (w/v) NaCl aqueous solution, making the concentration of the bacteria be about 108 cfu/mL, as the bacteria liquid to be induced (bacteria suspension).
2. High Pressure Carbon Dioxide Treatment
   Experimental group: the bacteria liquid is subjected to the high pressure carbon dioxide treatment using a self-designed high pressure carbon dioxide sterilization equipment (model: CAU-HPCD-1, a high density of carbon dioxide sterilization equipment, disclosed in the patent ZL200520132590.X); the specific steps are: 20 mL of bacteria liquid to be induced (bacteria suspension) was put into a glass bottle, and sealed with a sealing film; the bacteria liquid was put into a reaction kettle, and treated with HPCD at a pressure of 5 MPa and a temperature of 25° C., with the pressure being held for 40 min; the kettle was immediately depressurized when above treating parameters were achieved; the induced bacteria liquid was thus obtained.
   Control group: the bacteria liquid to be induced was not treated with high pressure carbon dioxide, but only placed at 25° C. for 40 min.
II. Detection
   Method for determining the number of viable bacteria: the PI/SYTO 9 double staining method was used; specific steps are: a proportioned dye mixture (volume ratio of PI:SYTO 9 was 1:1) was mixed with the induced bacteria liquid or the control in a ratio of 3:1000, and incubated at room temperature for 15 min in the dark after evenly mixed; after incubation, the bacteria were observed and counted under a fluorescence microscope (1000×), typically 10 fields were selected, and one sample was repeated twice.
   Method for determining the number of culturable bacteria: the plate counting method was used; specific steps: refer to the method of GB 4789.2-2010, the induced bacteria liquid was serially (1:10) diluted with 0.85% NaCl; 1 mL of diluted sample of each of 3 successive dilutions was aspirated into a sterilized dish, respectively, and 20 mL of TSA culture media were poured thereto and shaken well; after the culture media were solidified, the plates were turned upside down and cultured in an 37° C. incubator for 24 h, and then the numbers of bacterial colonies were recorded.
   The numbers of viable bacteria and culturable bacteria of experimental group and control group were detected using the above methods respectively, and thereby the number of bacteria in viable but nonculturable state (the number of viable bacteria–the number of culturable bacteria) was calculated.
   Whether the bacterium entered into the viable but nonculturable state was detected. When the number of culturable bacteria was zero but the number of viable bacteria was not, the bacterium was considered as being in the viable but nonculturable state.
   The results were as follows: the number of viable bacteria of the induced bacteria liquid of the experimental group was $10^{6.79}$ cfu/mL; the number of culturable bacteria of the induced bacteria liquid was 0; the number of bacteria entering into the viable but nonculturable state was $10^{6.79}$ cfu/mL.
   The number of culturable bacteria of the control group was still about $10^8$ cfu/mL, which was basically considered as no bacterium entering into the viable but nonculturable state.
   Thus, it can be seen that, in the present methods, *E. coli* O157:H7 in the viable but nonculturable state was obtained when being induced with high pressure carbon dioxide for 40 min, while the method of oligotrophy combined with low temperatures currently used needs one month to obtain viable but nonculturable cells. Therefore, the methods of the present invention may induce bacteria to enter into the viable but nonculturable state rapidly.

EXAMPLE 2

Inducing Bacterium to Enter into a Viable but Nonculturable State

I. Induction by High Pressure Carbon Dioxide.
1. Preparation of Bacterial Suspension.
   The method was the same as that of step 1 of I in Example 1.
2. High Pressure Carbon Dioxide Inducement.
   The method was substantially the same as that of step 2 of I in Example 1, only changing the treatment temperature to 31° C., and the pressure holding time to 30 min; and the induced bacteria liquid was obtained.
II. Detection
   The method was the same as that of II in Example 1.
   The results were as follows: the number of viable bacteria of the induced bacteria liquid of the experimental group was $10^{6.89}$ cfu/mL; the number of culturable bacteria of the induced bacteria liquid was 0; thus, the number of bacteria entering into the viable but nonculturable state was $10^{6.89}$ cfu/mL.
   The number of culturable bacteria of the control group was still about $10^8$ cfu/mL, which was basically considered as no bacterium entering into the viable but nonculturable state.
   Thus, it can be seen that, *E. coli* O157:H7 in the viable but nonculturable state was obtained when being induced with high pressure carbon dioxide for 30 min in the methods of the present invention.
   As compared with Example 1, the time for inducing *E. coli* O157:H7 to enter into the viable but nonculturable state by high pressure carbon dioxide was more shortened in the present Example, and the number of bacteria in the viable but nonculturable state obtained was close to that of Example 1.

EXAMPLE 3

Inducing Bacterium to Enter into the Viable but Nonculturable State Rapidly

I. Induction by High Pressure Carbon Dioxide.
1. Preparation of Bacterial Suspension.
   The method was the same as that of step 1 of I in Example 1.
2. High Pressure Carbon Dioxide Inducement.
   The method was substantially the same as that of step 2 of I in Example 1, only changing the treatment temperature to 37° C., and the pressure holding time to 25 min; and then the induced bacteria liquid was obtained.

The results were as follows: the number of viable bacteria of the induced bacteria liquid of the experimental group was $10^{5.72}$ cfu/mL; the number of culturable bacteria of the induced bacteria liquid was 0; thus, the number of bacteria entering into the viable but nonculturable state was $10^{5.72}$ cfu/mL.

The number of culturable bacteria of the control group was still about $10^8$ cfu/mL, which was basically considered as no bacterium entering into the viable but nonculturable state.

Thus, it can be seen that, in the methods of the present invention, *E. coli* O157:H7 in the viable but nonculturable state was obtained when being induced with high pressure carbon dioxide for 25 min.

As compared with Examples 1 and 2, the time for inducing *E. coli* O157:H7 to enter into the viable but nonculturable state by high pressure carbon dioxide was shorter in the present Example, while the number of bacteria in the viable but nonculturable state obtained was lower than that of Examples 1 and 2.

Industrial Application

It is demonstrated by the experiments of the present invention that a method for inducing bacteria to enter into viable but nonculturable state is developed by the present invention. By using high pressure carbon dioxide treatment, the bacterium can be promoted to enter into the viable but nonculturable state quickly within 1 h; and thus the speed of preparing bacteria in viable but nonculturable state and the study progress of bacteria in viable but nonculturable state are increased by the method of the present invention.

What is claimed is:

1. A method of inducing a target bacterium to enter into a viable but nonculturable state, comprising: subjecting the target bacterium to high pressure carbon dioxide treatment so as to make the target bacterium enter into the viable but nonculturable (VBNC) state, wherein conditions of the high pressure carbon dioxide treatment comprise a pressure of 5-7 MPa, a temperature of 25-37° C., and a time of 5-60 min, wherein the target bacterium is a Gram-negative bacterium.

2. The method according to claim 1, wherein conditions of the high pressure carbon dioxide treatment are as follows:
    a pressure of 5 MPa, a temperature of 25° C., and a time of 40 min;
    a pressure of 5 MPa, a temperature of 31° C., and a time of 30 min; or
    a pressure of 5 MPa, a temperature of 37° C., and a time of 25 min.

3. The method according to claim 1, wherein prior to the high pressure carbon dioxide treatment, the method further comprises: washing and suspending the target bacterium to obtain a bacteria suspension.

4. The method according to claim 3, wherein a physiological saline is used in both the washing and the suspending, and the physiological saline is a 0.85% (w/v) NaCl aqueous solution.

5. The method according to claim 1, wherein the target bacterium is in exponential phase.

6. The method according to claim 5, wherein the target bacterium is *Escherichia coli*.

7. The method according to claim 5, wherein the target bacterium is *Escherichia coli* O157:H7.

* * * * *